(12) United States Patent
Nguyen et al.

(10) Patent No.: US 11,376,446 B2
(45) Date of Patent: Jul. 5, 2022

(54) RADIATION THERAPY SYSTEMS AND METHODS USING AN EXTERNAL SIGNAL

(71) Applicants: Doan Trang Nguyen, Meadowbank (AU); Paul Keall, Greenwich (AU)

(72) Inventors: Doan Trang Nguyen, Meadowbank (AU); Paul Keall, Greenwich (AU)

(73) Assignee: SEETREAT PTY LTD, Greenwich (AU)

( * ) Notice: Subject to any disclaimer, the term of this patent is extended or adjusted under 35 U.S.C. 154(b) by 0 days.

(21) Appl. No.: 16/978,825

(22) PCT Filed: Mar. 8, 2019

(86) PCT No.: PCT/AU2019/050206
§ 371 (c)(1),
(2) Date: Sep. 8, 2020

(87) PCT Pub. No.: WO2019/169450
PCT Pub. Date: Sep. 12, 2019

(65) Prior Publication Data
US 2021/0038916 A1   Feb. 11, 2021

(30) Foreign Application Priority Data

Mar. 8, 2018 (AU) .............................. 2018900761

(51) Int. Cl.
*A61B 6/00* (2006.01)
*A61N 5/10* (2006.01)

(52) U.S. Cl.
CPC ......... *A61N 5/1037* (2013.01); *A61N 5/1045* (2013.01); *A61N 5/1049* (2013.01); *A61N 5/1067* (2013.01); *A61N 5/1068* (2013.01); *A61N 5/1069* (2013.01); *A61N 5/1071* (2013.01); *A61N 5/1081* (2013.01); *A61N 2005/1061* (2013.01); *A61N 2005/1072* (2013.01)

(58) Field of Classification Search
None
See application file for complete search history.

(56) References Cited

U.S. PATENT DOCUMENTS

| | | | | |
|---|---|---|---|---|
| 2008/0281192 | A1* | 11/2008 | Keall | A61B 6/12 600/426 |
| 2010/0016712 | A1* | 1/2010 | Bartal | A61B 6/5247 600/425 |
| 2018/0056090 | A1* | 3/2018 | Jordan | A61N 5/103 |

* cited by examiner

*Primary Examiner* — Hoon K Song
(74) *Attorney, Agent, or Firm* — WCF IP

(57) ABSTRACT

There is disclosed a method for estimating the position of a target in a body of a subject. The method includes, receiving an external signal that is related with motion of the target; and using a model of a correlation between the external signal and the motion of the target to estimate the position of the target, wherein said position estimation includes an estimate of three dimensional location and orientation of the target. The method further includes periodically receiving a 2-dimensional projection of the target; and updating the model of correlation between the external signal and the motion of the target based on a comparison of the estimated position of the target and the 2-dimensional projection of the target. The method is used in guided radiation therapy.

19 Claims, 14 Drawing Sheets

RADIATION THERAPY SYSTEMS AND METHODS USING AN EXTERNAL SIGNAL

FIELD OF THE INVENTION

The present disclosure relates to systems and methods for use in relation to guided radiation therapy systems. In one form there is disclosed a system and method for use in motion tracking of target in a guided radiation therapy system.

BACKGROUND OF THE INVENTION

Radiation therapy is a treatment modality used to treat localised tumours. It generally involves producing high energy megavoltage (MV) and conformal beams of x-rays to the target (tumour) using a medical linear accelerator. The radiation interacts with the tissues to create double strand DNA breaks to kill tumour cells. Radiation therapy requires high precision to deliver the dose to the tumour and spare healthy tissue, particularly that of organs surrounding the tumour. Each treatment is tailored on a patient-by-patient basis.

In current radiation therapy, image guided radiation therapy (IGRT) is routinely applied at the start of treatment to align the target with its planned position. However, tumours in the thorax, abdomen and pelvis are not static during treatment. Patients undergoing radiotherapy treatment are subject to movement both in the setup on the treatment bed and by way of organ and tumour motion during treatment delivery.

Increasing evidence suggests that such intrafractional tumour motion corrections should be applied for both tumour translations and tumour rotations. Retrospective post-treatment calculations of tumour rotations have shown that the rotations could be significant for both prostate and lung tumours. Tumour motion can occur in six degrees of freedom (6DoF) that is, rotational and translational movements can occur about and along three axes. Tumour motion during treatment can cause large radiation doses to be delivered to critical structures and healthy tissue, leading to suboptimal dosimetry (dose coverage outside the tumour). In this regard, dosimetrically, uncorrected prostate rotations of 15° can result in a 12% under dose to the tumour.

Motion management in radiation therapy has thus become vital in delivering accurate dose coverage and limiting toxicities to healthy tissue. With the increase of using stereotactic body radiation therapy (SBRT), which delivers high doses in small fractions within a small field size (small X-ray beam size), motion management becomes extremely significant to allow conformal high doses to be delivered to the target site whilst sparing healthy tissue.

A number of different intrafraction real-time guidance methods have been used during prostate cancer treatments. Systems such as CyberKnife (Accuray, Sunnyvale, Calif.) and the real-time tracking radiotherapy (RTRT) system use real-time kilovoltage (kV) images from two (CyberKnife) or four (RTRT system) orthogonal room-mounted imagers to track the prostate position based on 10 segmented positions of implanted fiducial markers. Calypso (Varian, Palo Alto, Calif.) and RayPilot (Micropos, Gothenburg, Sweden) utilise implanted electromagnetic transponders, transmitting positional signals to an external receiver. Emerging real-time guidance technologies include ultrasonography and integrated magnetic resonance imaging (MRI)-radiation therapy systems. However, common to all these methods is the drawback that they need additional dedicated and typically expensive equipment to perform the real-time guidance.

Ideally, real-time image guidance would be performed using a standard linear accelerator (linac) without relying on additional hardware. Since most modern linear accelerators have a kV x-ray imager system, mounted orthogonally to the treatment beam, a number of algorithms have been proposed for the purpose of estimating the target's position in 3D based on its location on a 2D x-ray image, which has been acquired using the linear accelerator's gantry mounted kV x-ray imager system. However, the target position on the kV imager only contains 2D information, making accurate position determination complex.

One new approach to monitoring patient motion has been developed named Kilovoltage Intrafraction Monitoring (KIM). KIM is a real-time image guidance technique that utilises existing radiotherapy technologies found in cancer care centres (i.e. on-board x-ray images). KIM exploits fiducial markers implanted inside the tumour (organ) and reconstructs their location by acquiring multiple images of the target using the on-board kilovoltage (KV) beam which is a low energy X-ray imager and determines any motion in the left-right (LR), superior-inferior (SI), and anterior-posterior (AP) directions. KIM Tracking has also been developed which dynamically modifies the multi leaf collimator (MLC) position while delivering the treatment dose base of the tumour position reconstructed by KIM. KIM-gated radiation therapy is currently used to treat prostate cancer patients at multiple cancer centres could also be expanded to treat lung cancer patients in the near future. In KIM, tumour motion is monitored in real-time while both the MV beam is delivering the treatment dose and the KV beam is imaging the tumour target. If significant motion away from the treatment beam occurs the treatment is paused and the patient is repositioned before the treatment is continued.

One drawback to using kV imaging during treatment is the additional radiation dose to the patient due to continuous X-ray imaging. Cho et al. 2010 described a general framework allowing occasional kV imaging during treatment by utlising the continuous signal from external surface or volumetric signal. The source of the external signal can come from either optical surface monitoring devices such as RPM (Varian), AlignRT (VisionRT), or volumetric measurements such as the bellows belt (Philips Healthcare). All of these devices are common in a modern radiotherapy department. This method allows X-ray images to be taken less often and thereby significantly reduces imaging dose to the patient. However, the method proposed by Cho et al. (2010) only computes 3D target translation and not rotation so is of limited utility.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect of the disclosure there is provided method for estimating the position of a target in a body of a subject. The method can include: receiving an external signal that is related with motion of the target; using a model of the correlation between the external signal and the motion of the target to estimate the position of the target, wherein said position estimation includes an estimate of three dimensional location and orientation of the target; periodically receiving a 2-dimensional projection of the target; and updating the model of correlation between the external signal and the motion of the target based on a comparison of the estimated position of the target and the 2-dimensional projection of the target.

Periodically receiving a 2-dimensional projection of the target, can include receiving a 2-dimensional projection of the target at any one of the following intervals: 0.1 s, 1 s, 3 s, 10 s, 30 s, an interval greater than 0.1 s, an interval greater than 1 s, an interval greater than 3 s, an interval greater than 10 s, an interval greater than 30 s.

The method can further include determining the correlation between the external signal and the motion of the target to enable estimation the position of the target by: receiving a series of 2-dimensional projections captured at a rate equal to or higher than the periodically received 2-dimensional projection of the target; receiving an external signal that overlaps in in time with at least part of the received series of 2-dimensional projections; and determining a correlation between the external signal at a time (t) and a three dimensional location and orientation of the target from a plurality of said 2-dimensional projections.

The successive projections in the series of 2-dimensional projections may be captured at an interval being any one of the following: an interval less than 0.1 s, 0.1 s, an interval less than 1 s.

Preferably the external signal represents respiration of the subject. The external signal representing respiration can be output from any suitable monitoring device such as for example, an optical surface monitoring device; volumetric or spirometric measuring device. In one example it is a bellows belt.

The 2-dimensional projection is preferably an x-ray image of at least part of a subject and includes the target.

A three dimensional location and orientation of the target from a plurality of said 2-dimensional projection may be determined by: identifying one or more markers or landmarks positioned with respect to the target to facilitate identification of the target in a 2-dimensional projection. Preferably the at least three markers are identified. Landmarks can include intrinsic anatomy (such as tumour or bone) that can be identified in the 2-dimensional projection. Preferably 3 or more unique landmarks can be identified such that translation and rotation motion can be computed as described herein.

Also disclosed is a guided radiation therapy method in which at least one beam of radiation is directed at a target, said method including: estimating the position of the target using an embodiment of the method(s) of said first aspect of the disclosure, and directing the beam based on the estimated position. The method can further include, tracking the target by successively performing a method of estimating the position of the target an embodiment of the method(s) first aspect of the disclosure, and directing the beam at the target based on said tracking.

Directing the beam based on the estimated portion may include adjusting or setting one or more of the following system parameters:
  at least one geometrical property of said at least one emitted beam;
  a position of the target relative to the beam;
  a time of emission of the beam,
  an angle of emission of the beam relative to the target about the system rotational angle.

A system for guided radiation therapy is also disclosed. The system can include: A radiation source for emitting at least one treatment beam of radiation; An imaging system arranged to generate a succession of images comprising a two dimensional projection of a field of view and in which the location of the target may be identified; A monitoring system arranged to sense from the subject a parameter that is related with motion of the target, and output an external signal that is related with motion of the target; and a control system to direct the at least one treatment beam at the target, wherein said beam control system is configured to:
  receive images from the imaging system and the external signal; and estimate the position of the target using a method according to a method of the first aspect of the disclosure; and
  adjust the system to direct the at least one beam at the target.

The radiation source is configured to direct a treatment beam along a first beam axis, and the imaging system includes a second radiation source configured to emit at least one imaging beam along a second beam axis that is orthogonal to the first direction and a radiation detector configured to detect radiation transmitted through the target to generate a projection of said at least one imaging beam in a plane normal to the direction of emission of the at least one imaging beam.

The system may further rotate the radiation source and imaging system about a system rotational axis that is orthogonal to the first and second direction to enable sequential treatment and imaging of the subject at different angular positions about the system rotational axis.

The system may further include a support platform on which a subject of radiation therapy is supported during treatment, at a location such that the centroid of the target is substantially aligned with the intersection between the system rotational axis, and the first and second beam axes.

The control system may control one or more of:
  at least one geometrical property of said at least one emitted beam;
  a position of the target relative to the beam;
  a time of emission of the beam, an angle of emission of the beam relative to the target about the system rotational angle. As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

In each of FIGS. 6 to 10 the top set of of plots shows the case with the largest standard deviation of error (VMAT 1.6° s$^{-1}$) at the highest interval between imaging update (30 s) and the bottom group of plots shows the case with the lowest standard deviation of error (VMAT 6° s$^{-1}$) at the most frequent imaging update (0.1 s).

DETAILED DESCRIPTION OF THE EMBODIMENTS

Figure 1:
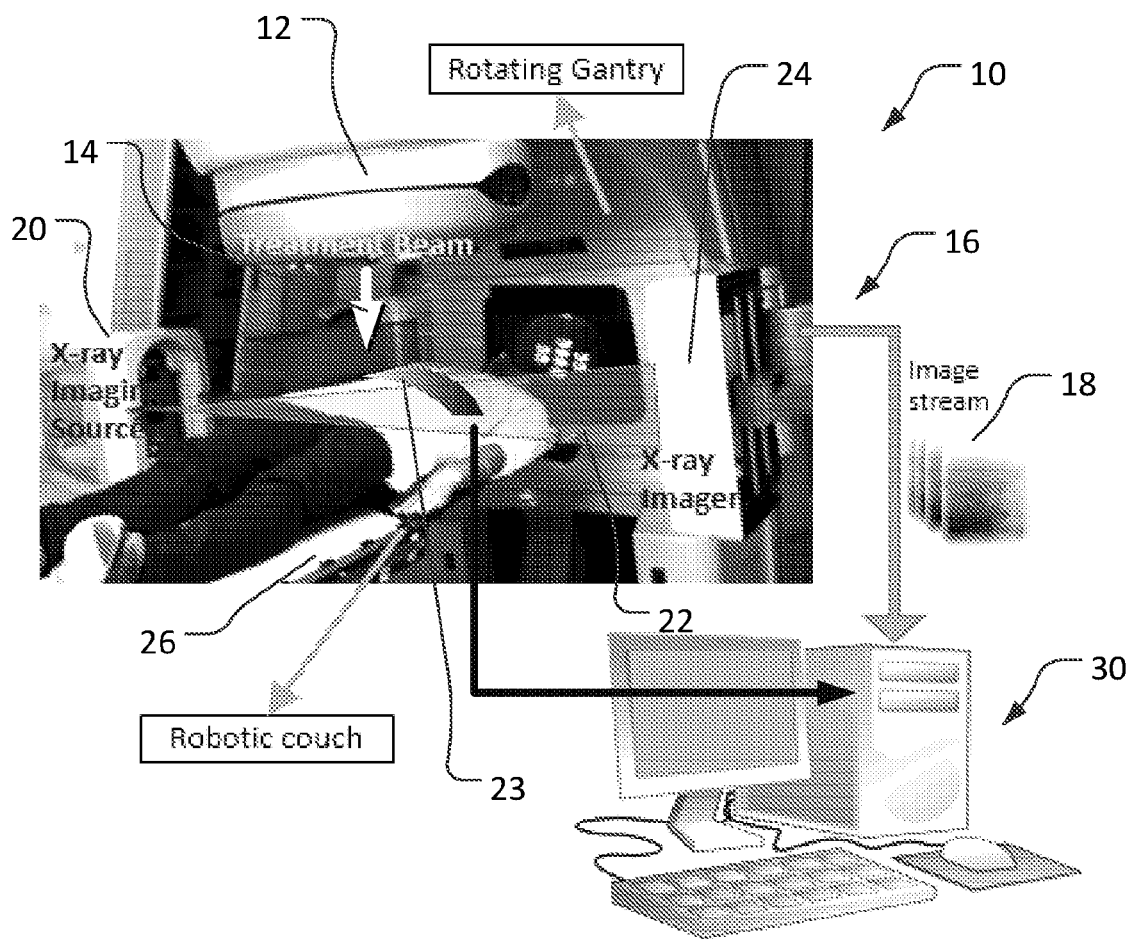
FIG. 1 illustrates a schematic representation of a system configured to implement an embodiment of the present disclosure.

FIG. 1, depicts a system for image guided radiation therapy able to implement an embodiment of the methods described herein. The system 10 includes:

A radiation source 12 for emitting at least one treatment beam of radiation. The radiation source emits the treatment beam 14 along a first beam axis towards the patient being treated. Typically the radiation source 12 will comprise a linear accelerator emitting megavolt x-rays.

An imaging system 16 arranged to generate a succession of images 18 comprising a two dimensional projection of a field of view and in which the location of the target may be identified. The imaging system 16 includes a second radiation source 20 that emit at least one imaging beam 22 along a second beam axis. The imaging beam 22 will be transmitted in a direction orthogonal to the treatment beam 14. The imaging beam is transmitted through the patient (or at least through the region of the patient including the target) to a radiation detector 24 that is configured to detect radiation transmitted through the target. The spatial intensity of the received radiation is converted to an x-ray image that is a projection of said at least one imaging beam in a plane normal to the direction its emission. Typically the imaging system will be a kilovolt imaging system built into the linear accelerator. In embodiments of the present disclosure the imaging system is arranged to only intermittently emit its imaging beam, to thereby reduce the patient's radiation exposure compared to continuous imaging. The rate of imaging can vary depending on requirements or system configuration but will typically have an imaging interval between 0.1 s to 60 s. Some embodiments may have a longer imaging interval.

A support platform 26 (e.g. a bed) on which the subject of the radiation therapy is supported during treatment. Support platform is repositionable relative to the imaging system and radiation source so that the patient can be positioned with the centre of the target (e.g. tumour) located as near as possible to the intersection between the first and second beam axes.

A respiratory monitor 23 which generates a signal indicative of the respiration of the patient. The respiratory monitor can generate a continuous signal from external surface or volumetric signal. The source of the external signal can come from, any suitable source including but not limited to optical surface monitoring devices; such as RPM (Varian, Palo Alto, Calif.), Optical Surface Monitoring System (OSMS) (Varian, Palo Alto, Calif.), AlignRT (VisionRT, London, UK), Catalyst (C-RAD, Uppsala, Sweden)); or volumetric measurements, such as the bellows belt (Philips Healthcare). A control system 30 that controls the parameters of operation of the radiotherapy system. Generally speaking the control system 30 is a computer system comprising one or more processors with associated working memory, data storage and other necessary hardware, that operates under control of software instructions to receive input data from one or more of a user, other components of the system (e.g. the imaging system & respiratory monitor 23), and outputs control signals to control the operation of the radiation therapy system. Amongst other things the control system 30 causes the radiation source 12 to direct its least one treatment beam at the target. To do this the control system receives images from the imaging system and estimates the motion of the target, then issues a control signal to adjust the system 10 to direct the treatment beam 14 at the target.

As will be appreciated by those skilled in the art, the radiation source 12, imaging system 16 and support platform 30 are common to most conventional image radiation therapy systems. Accordingly, in the conventional manner the radiation source 12, imaging system 16 can be rotatably mounted (on a structure commonly called a gantry) with respect to the patient support platform 30 so that they can rotate about the patient in use. The rotational axis of the gantry motion is typically orthogonal to the directions of the treatment beam and imaging beam (i.e. the first and second directions.) It enables sequential treatment and imaging of the patient at different angular positions about the system's gantry's axis.

As noted above, the control system 30 processes the respiratory signal from the respiratory monitor 23 and images received from the imaging system 16 and estimates the motion of the target, then issues a control signal to adjust the system 10 to direct the treatment beam at the target. The adjustment will typically comprise at least one of the following: changing a geometrical property of the treatment beam such as its shape or position, e.g. by adapting a multi-leaf collimator of the linac; changing the time of emission of the beam, e.g. by delaying treatment beam activation to a more suitable time; gating the operation of the beam, e.g. turning off the beam if the estimated motion is greater than certain parameters; changing an angle at which the beam is emitted relative to the target about the system rotational axes. The system 10 can also be adjusted so as to direct the treatment beam at the target by moving the patient support platform 26. Moving the support platform 26 effectively changes the position of the centroid of the target with respect to the position of the treatment beam 14 (and imaging beam).

In use the general method of operation in of the system 10 is as follows. The respiratory monitor 23 monitors the breathing of the patient. The radiation source and imaging system rotates around the patient during treatment. The imaging system acquires 2D projections of the target separated by an appropriate time interval. Generally the target (tumour) will be marked by the placement of fiducial markers within or about the target. The positioning of the markers may be such that the centroid of the markers lies at the centre of the target, but this is not strictly necessary. The control system 30 uses a determined correlation between the respiratory signal and target's location and orientation, and the periodically received 2D projections (e.g. kV X-ray images) to estimate the tumour's position. The control system therefore needs a mechanism for determining the correlation that exists and then performing ongoing estimating the target's location and orientation in 3-dimensions.

Thus, in the preferred embodiment, tracking as performed on the basis of an external signal and occasional imaging information. The disclosed method utilises the inherent link between the external respiratory signal and the internal tumour motion, determined during a learning phase of operation.

A method for estimating the 6DoF motion from a one dimensional external respiratory signal and intermittent 2D projections of a target using a least square method will now be described. However, it should be noted that with the use of other types of respiration monitors multiple-dimensional respiration signals could be acquired and used. Then, we describe a VMAT simulation used to comprehensively evaluate the method, based on patients lung data, acquired using the Calypso electromagnetic system (Varian, Calif., USA) at the Northern Sydney Cancer Centre (St Leonard, Sydney, Australia). Throughout this description the IEC 61217 coordinate system is used to describe the patients' motion relative to the treatment beam. According to this coordinate system, the motion in the x-direction corresponds to the Left-Right (LR) direction, the y-direction corresponds to the Superior-Inferior (SI) direction and the z-direction corresponds to the Anterior-Posterior (AP) direction of a patient in the treatment room in the head-first supine orientation.

In the present description the concept of determining or estimating the position of a target refers to determining an offset in the position and rotation of the target from a reference position and rotation. In the example below the reference positon is labelled $M_{ref}$.

Learning Phase

The method begins with a learning phase. The relationship between the internal target motion and the external respiratory signal s(t) can be defined as a composite linear correlation:

$$(\hat{T}_r; \hat{\varphi})(t) = \begin{pmatrix} \hat{T}_{rx} \\ \hat{T}_{ry} \\ \hat{T}_{rz} \\ \hat{\alpha} \\ \hat{\beta} \\ \hat{\gamma} \end{pmatrix} = \begin{pmatrix} a_x \\ a_y \\ a_z \\ a_\alpha \\ a_\beta \\ a_\gamma \end{pmatrix} \cdot s(t) + \begin{pmatrix} b_x \\ b_y \\ b_z \\ b_\alpha \\ b_\beta \\ b_\gamma \end{pmatrix} \cdot s(t-\lambda) + \begin{pmatrix} c_x \\ c_y \\ c_z \\ c_\alpha \\ c_\beta \\ c_\gamma \end{pmatrix} = a \cdot s(t) + b \cdot s(t-\lambda) + c \quad (1)$$

where $\hat{T}_r = (\hat{T}_{rx} \ \hat{T}_{ry} \ \hat{T}_{rz})^T$ is the translation vector around the [x; y; z] axes of the transformation equation, respectively and the angles $\varphi = (\alpha\beta\gamma)^T$ are the rotations angles around the [x; y; z] axes, respectively. In the Equation(1), the parameter $\lambda$ is a time-augmented parameter, following the work of Ruan et al. (2008).

Ruan, D., Fessler, J. A., Balter, J. M., Berbeco, R. I., Nishioka, S. & Shirato, H. (2008), 'Inference of hysteretic respiratory tumor motion from external surrogates: A state augmentation approach', Phys Med Biol 53, 2923-2936.

Together, the parameters $\hat{T}_r(t)$ and $\varphi(t)$ can be used to calculate the linear transformation between the original orientation and position $M_{ref}$ of the target and the current position and orientation M(t) of the target:

$$M(t) = \begin{pmatrix} x_1 & x_2 & \dots & x_n \\ y_1 & y_2 & \dots & y_n \\ z_1 & z_2 & \dots & z_n \end{pmatrix} (t) = \begin{pmatrix} x \\ y \\ z \end{pmatrix} (t) = R(t) \cdot M_{ref} + \hat{T}_r(t) \quad (2)$$

where:

$$R(t) = R_x(t)R_y(t)R_z(t) = \begin{pmatrix} \cos\beta\cos\gamma & -\cos\beta\sin\gamma & \sin\beta \\ \cos\alpha\sin\gamma + \sin\alpha\sin\beta\cos\gamma & \cos\alpha\cos\gamma - \sin\alpha\sin\beta\sin\gamma & -\sin\alpha\cos\beta \\ \sin\alpha\sin\gamma - \cos\alpha\sin\beta\cos\gamma & \sin\alpha\cos\gamma + \cos\alpha\sin\beta\sin\gamma & \cos\alpha\cos\beta \end{pmatrix} \quad (3)$$

Additionally, if the current orientation and position of the target M(t) is estimated from Eq.(1) as $\hat{M}(t)$, then we can estimate the projected positions of $\hat{M}(t)$ using the projection equation:

$$\hat{P}(\hat{M}(t)|\theta) = \begin{pmatrix} \hat{u} \\ \hat{v} \end{pmatrix} = \frac{SID}{SAD - (\hat{x} \cdot \cos\theta + \hat{z} \cdot \sin(\theta))} \begin{pmatrix} \hat{x} \cdot \sin\theta - \hat{z} \cdot \cos(\theta) \\ \hat{y} \end{pmatrix} \quad (4)$$

with:
$(\hat{u} \ \hat{v})^T$: the position of the target on the imager,
SID: the X-ray Source to Imager Distance of the system,
SAD: the X-ray Source to Axis (Isocentre) Distance of the system.

Thus, after a learning phase where the actual projected positions $(\hat{u} \ \hat{v})^T$ are detected, the parameters a, b and c of the correlation equation (Eq.1) can be found by minimizing the sum of the distances between the estimated positions $(\hat{u} \ \hat{v})^T$ and the actual projected positions over F number of imaging frames:

$$(a, b, c) = \text{argmin} \left\| \sum_{f=0}^{f=F} \sum_{n=1}^{n=N} |u_f^n - \hat{u}_f^n| + |v_f^n - \hat{v}_f^n| \right\|_2 \quad (5)$$

where N is the number of points or markers representing the target M. In order to find a unique orientation R for the target M, the minimum number of points required is 3. However, the state augmentation parameter $\lambda$ in Eq.1 cannot be found with the aforementioned minimisation process. In this example $\lambda$ is found iteratively by choosing the $\lambda$ parameter that produces the smallest mean estimation error over the learning period using the cost function in Eq.5. The algorithm below shows an exemplary implementation of the 6D-IEC algorithm at the end of the learning phase. In this implementation, the state augmentation parameter $\lambda$ is an integer number of frames. For the in silico simulation described below, each frame corresponds to 100 ms.

```
for λ_i = 0:N
    [~, ~, ~, ~, E(i)] ← compute6DIEC(s_t, (u v)^T, M_ref, λ_i);
end for
λ = λ_i s.t. min(E);
[a, b, c, estimated6DoF, E] ← compute6DIEC(s_t, (u v)^T, M_ref, λ);
function compute6DIEC(s_t, (u v)^T, M_ref, λ)
    % Compute the augmented respiratory signal
    s_{t-λ} ← s_t(t - λ);
    %Define Convergence threshold
    T = 10^-3;
    % Initialise optimisation seeds
    [a_0, b_0, c_0] = 0;
    while |E - E_temp| > T
        % E: sum of squared estimation errors
        E ← E_temp;
        % Optimise to solve for [a, b, c](equations (1)–(5))
        [a, b, c, E_temp] ← NLLS(s_t, s_{t-λ}, (u v)^T, M_ref, seeds = [a_0, b_0, c_0]);
        % Randomly move the seeds to reduce the probability of local minima
        [a_0, b_0, c_0] ← [a, b, c] + 0.1 * rand([0 : 1]);
    end while
    estimated6DoF ← a * s_t + b * s_{t-λ} + c;
    return [a, b, c, estimated6DoF, E];
end function
```

Tracking Phase

Once learning is complete the tracking phase can begin. During the tracking phase the correlation parameter is known, thus, the current tumour position can be estimated as soon as the signal s(t) is available. Tracking continues by receiving the external signal and optionally processing it, e.g. by down sampling etc. This is used as an input to the estimation framework. In order to ascertain the estimation framework model is up to date, an update is occasionally required. This can be done using a current projection data, i.e. a recently captured 2D projection of the subject that shows the position of the target. The location of the fiducial markers is determined and the tumour position and orientation estimated. However, the full model cannot be built using the occasional projection data because the sampling frequency differs between the learning phase and tracking phase. During the tracking phase, the correlation model is only updated for the linear component a and the static shift component c but not the state augmentation component b. This process can be summarised as follows:

Use a model of the correlation between the external signal (e.g. a respiratory signal) and the motion of the target to estimate the position of the target.

Periodically receive a 2-dimensional projection of the target (e.g. from a kV imager mounted on the treatment gantry).

If the model output does not match the projection data to a sufficient extent, update the model of the correlation between the external signal and the motion of the target.

The correlation model can be determined prior to beginning tracking during a learning phase which involves:

Receive a series of 2-dimensional projections (e.g. x-ray images) that contain the target)

Receive the external signal (e.g. respiratory signal) and determine a correlation between it and the three dimensional location and orientation of the target as defined by the images.

Figure 2:
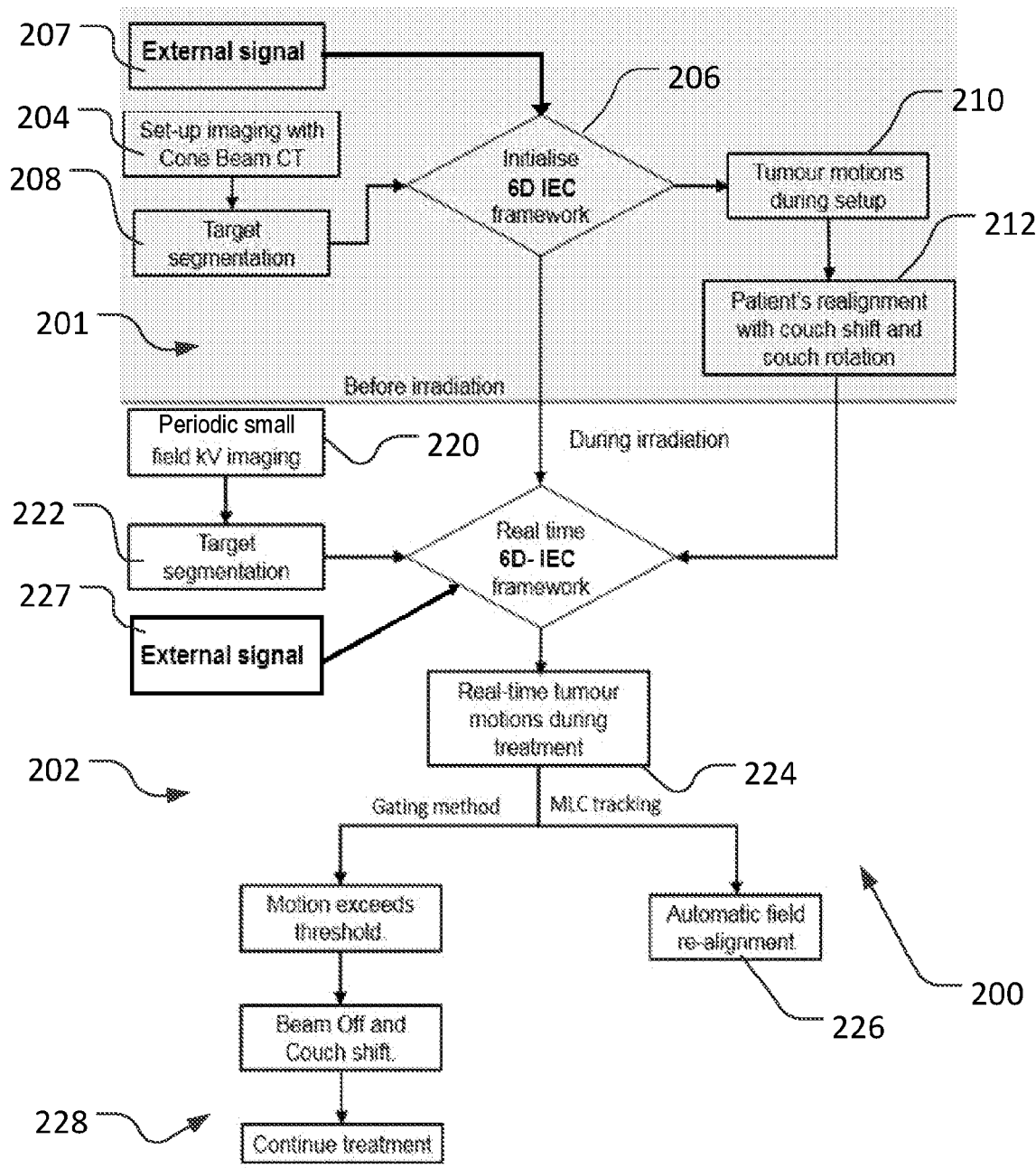
FIG. 2 is a flowchart of a guided radiation therapy process according to an embodiment of the present disclosure.

FIG. 2 illustrates a method of guided radiation therapy in which the process described above can be used. The methods of guided radiation therapy are similar to those followed by Huang et al. 2015 (Huang, C.-Y., Tehrani, J. N., Ng, J. A., Booth, J. T. & Keall, P. J. 2015. Six Degrees-of-Freedom Prostate and Lung Tumour Motion Measurements Using Kilovoltage Intrafraction Monitoring. Int J Radiat Oncol Biol Phys, 91, 368-375;); and Keall et al. 2016 (Keall, P. J., Ng, J. A., Juneja, P., O'brien, R. T., Huang, C.-Y., Colvill, E., Caillet, V., Simpson, E., Poulsen, P. R., Kneebone, A., Eade, T. & Booth, J. T. 2016. Real-Time 3D Image Guidance Using a Standard LINAC: Measured Motion, Accuracy, and Precision of the First Prospective Clinical Trial of Kilovoltage Intrafraction Monitoring Guided Gating for Prostate Cancer Radiation Therapy. Int J Radiat Oncol Biol Phys, 94, 1015-1021) (the contents of which are each incorporated by reference for all purposes with the exception of the use of the motion tracking method described herein).

The process 200 can be divided into two phases, set up or the learning phased 201 and treatment 202. The learning phase 201 uses an imaging procedure 204, e.g. Cone Beam CT, before treatment to initialise 206 the parameters for the movement tracking framework (termed the 6D-IEC framework in this description). Target segmentation 208 is used to identify fiducial markers in the target during initialisation. The tumour motion is related with the external signal 207 generated by the patient monitoring device. The patient monitoring device can be any suitable device that outputs a signal that represents a parameter that is known to be related with tumour motion, such as a respiratory signal. Thus the patient monitoring device could be a Bellow Belt (Philips Medical Systems, Cleveland Ohio) or the like to measure breathing. The initialised framework can then be used to track target motion 210. In some cases 212 patient re-alignment may be necessary. After initialisation, the method moves to the treatment phase 202. During the treatment phase the treatment beam is activated and the target irradiated, movement tracking system will update the tumour's translational and rotational motion 224 in real-time using the external signal 227 and occasional small-field kV images 220. As explained above the position of the fiducial markers are identified, e.g. using target segmentation 222 and this data is used to check and possibly update the position estimation model. As will be described below is it possible to extend the imaging period during the treatment phase 202 from that used during learning 201. The results below show that the period between images taken with the kV imager may be 30 seconds or longer whilst still maintaining useful tracking of the target in 6DoF motion. This may greatly reduce radiation dose received from the target imager compared with rapid imaging of previous techniques. The field of view for the kV imaging during treatment can be reduced to encompass only the tumour and anticipated motion range+50% to reduce imaging dose to the surrounding anatomy.

Motions output by movement tracking method can be used to either or both of: (1) control adaptation of an automatic Multi-Leaf-Collimator (MLC) which will follow the motion of the tumours and adapt the treatment field to hit the tumour at its current position 226; or (2) gate the operation of the treatment beam 228. In the event that detected motion of the target exceeds a pre-set threshold, the treatment beam can be deactivated and the robotic couch moved to re-align the target with the treatment field, after which the treatment can continue. Gating can be automatic or manually performed by a technician in response to an alert issued by the system controller.

The effectiveness of the position estimation technique described herein can be seen in simulations the inventors have performed as set out below.

Evaluation with Simulations

To characterize the performance and retrospectively validate the illustrated embodiment, patient data were obtained from first-in-world multi-leaf collimator (MLC) tracking Stereotactic Ablative Body Radiotherapy (SABR) (NCT02514512). As of July 2017, seven patients had been treated with this technique. Six patients were treated with 48 Gy in 4 fractions and 1 patient with 50 Gy in 5 fractions.

The internal patients motion was obtained using electromagnetic transponders implanted around the patients tumour. Additionally, a respiratory Bellow belt (Philips Medical System, Cleveland, Ohio) was wrapped around the patients abdomen to monitor the patients' breathing pattern during treatment delivery. The belt was equipped with a strain gauge coupled with a sensor to record pressure variation induced by chest stretching during breathing.

Manual synchronisation between bellow respiratory signal (40 Hz) and the Calypso signal with 3 or more beacons (10 Hz) was performed using events such as short apnea or patient cough. 3 patients were treated prone while the other 3 patients were treated supine. Of the 29 fractions, data from 19 fractions were included in the ground-truth dataset Finally, 6DoF intrafraction tumour motion of each fraction was computed using the Calypso data using the Iterative Closest Point Algorithm (Tehrani et al. 2012). The positions and poses of the transponders at the beginning of each fraction where used as the reference positions.

In order to test the accuracy of the 6D-IEC algorithm in estimating 6DoF motion, for each patient trajectory in the ground-truth dataset, the ground-truth 3D positions of the markers were projected onto an imager using equation (4). The SAD and SID value were set at 1000 mm and 1800 mm, respectively. This projection step is to stimulate a realistic scenario during treatment in which radio-opaque implanted markers can be segmented from infraction kV images.

All simulation started with the gantry rotated from 180° at the speed of 6° per second (6 dps) for 60 s. This is to simulate the initial Cone Beam Computed Tomography (CBCT) procedure at the beginning of each fraction. The CBCT period is used as the learning phase for 6D-IEC to build the first correlation model (e.g. as illustrated at 201 of FIG. 2). Imaging rate was simulated at 10 Hz during CBCT phase.

Three clinical treatment scenarios were tested. In one scenario, the gantry speed is set at 1.6°/s to simulate VMAT lung SABR treatment with flattened filter. In the second testing scenario, the gantry speed is set at 6°/s to simulate lung SABR treatment without flattened filter. Excluding the CBCT learning period, each tested trace include between 4 to 5 minutes of intra-fraction motion. The third scenario was an Intensity Modulated Radiation Therapy (IMRT) with 5 fields were simulated following the initial 60 s CBCT. For these 5 fields IMRT treatment, the linac gantry angles (MV) were set at 250°, 310°, 0°, 60° and 110° with the delivery time for each field set at 40 s.

During the simulated treatment phase, for each gantry speed scenario, the 6D-IEC algorithm was evaluated for different imaging update interval during the tracking period, including: 100 ms, 1 s, 3 s, 10 s and 30 s. The respiratory signal was 40 s Hz.

Results

Figure 2B:
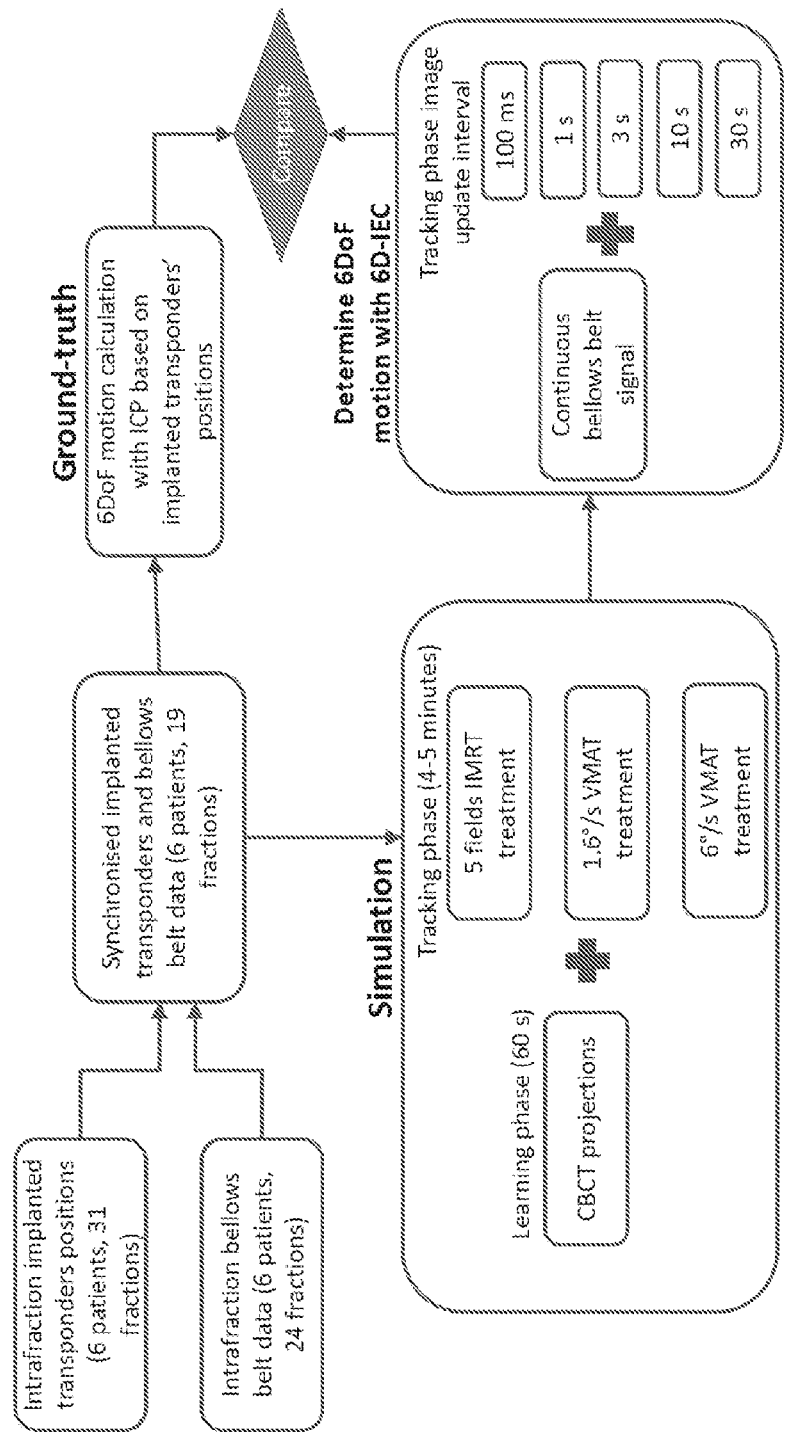
FIG. 2B is a schematic diagram of the method used to investigate the accuracy and precision of the an algorithm used in an embodiment of the present disclosure.

For this discussion, the translational motion is denoted by its axis of motion, e.g, translation motion in LR is denoted as LR. The rotational motion is denoted by an r before its axis of rotation, e.g rotation motion around the SI axis is denoted as rSI. This is simply for clarity in figures. To evaluate the accuracy and precision of 6D-IEC in estimating 6DoF motions, the 6D-IEC estimated motions were compared against the Calypso ground-truth 6DoF motions, as shown in FIG. 2B. The difference between 6D-IEC estimations and Calypso ground-truth are reported. Herein, we refer to this difference between 6D-IEC estimates and the ground-truth as error.

Figure 3A:
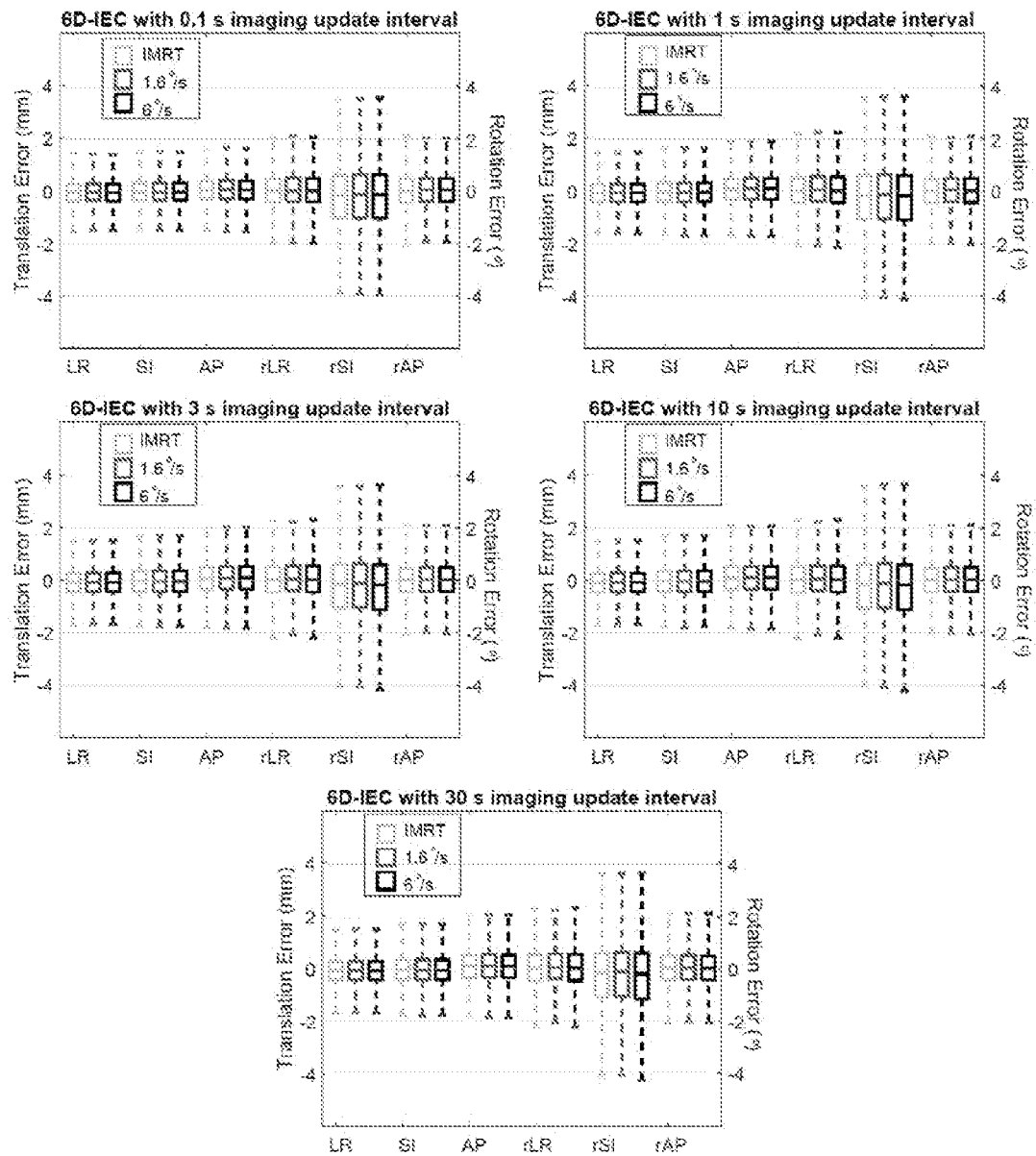
FIG. 3A illustrates boxplots of the error of 6D-IEC in estimating 6DoF lung tumour motions compared to the ground-truth motions from Calypso for all tested scenarios. The whisker in each boxplot contained 99:9% of the data.

FIG. 3A shows the boxplots of the error of 6D-IEC in estimating 6DoF lung tumour motions compared to the ground-truth motions from Calypso. Overall, in each of the imaging update intervals (0.1 s, 1 s, 3 s, 10 s, and 30 s) during the tracking phase, the errors in all 6DoFs are similar for both IMRT and VMAT treatment scenarios (gantry speed of 1.6 dps and 6 dps). As shown in the boxplot of FIG. 3, 99.9% of the errors for translations estimations with 6D-IEC is within ±2 mm of the ground-truth for imaging update interval of is or lower. The largest errors of translational motion estimation with 6D-IEC is in the AP direction. At the largest tested imaging update interval of 30 s, the 99.9% errors for AP are under 2.5 mm. For the rotations estimations, the largest errors are in the rotations around the SI axis with the 99.9% interval of the error are within ±4.2°. In all tested scenarios, the standard deviation of translational and rotational errors increases slightly as the imaging update interval increases.

Figure 3B:
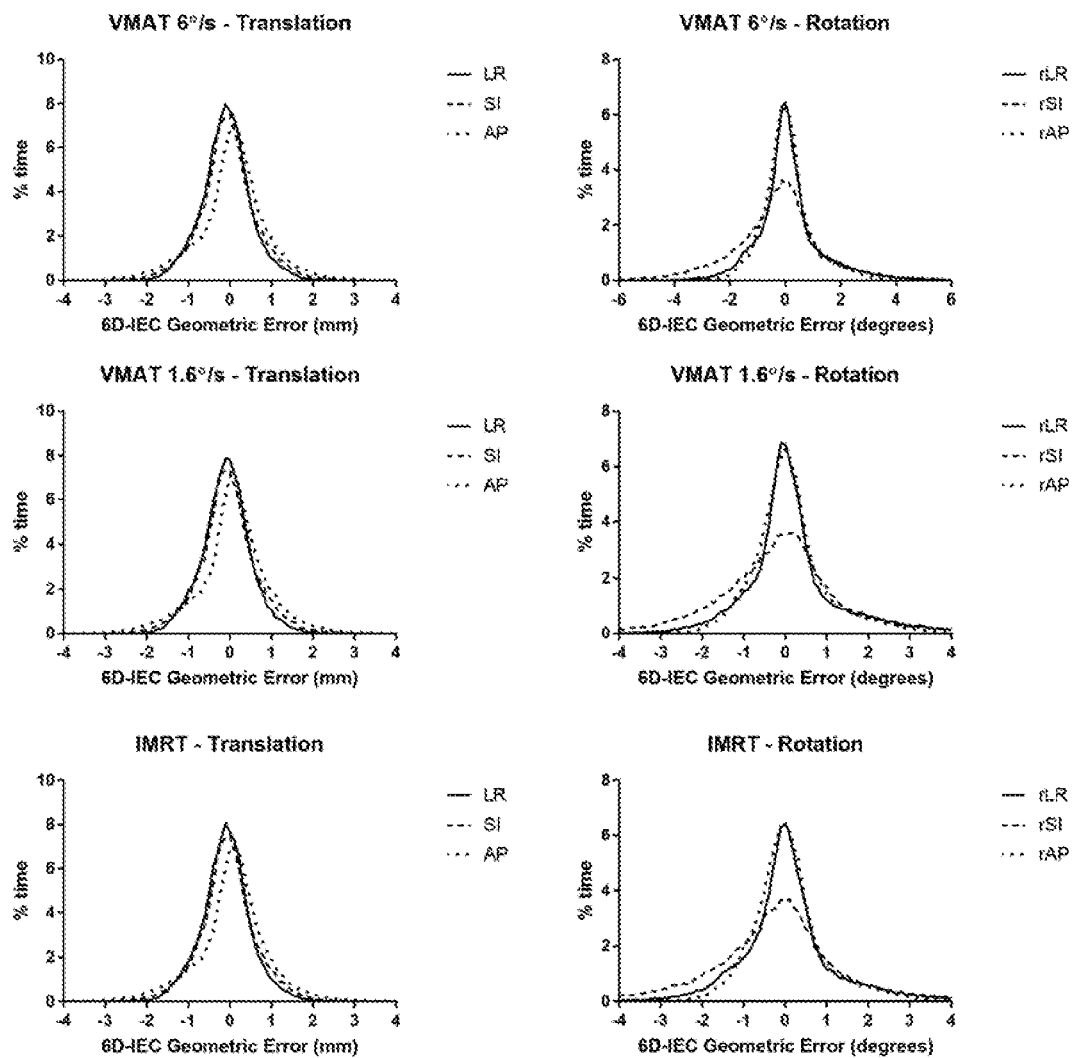
FIG. 3B show the frequency distribution (% of time) of geometric errors for all tests of FIG. 3A having an update interval of 30 s.

FIG. 3B shows the distribution of the geometric errors in all six degrees of freedom for the imaging updating interval of 30 s in FIG. 3A.

Figure 4A:
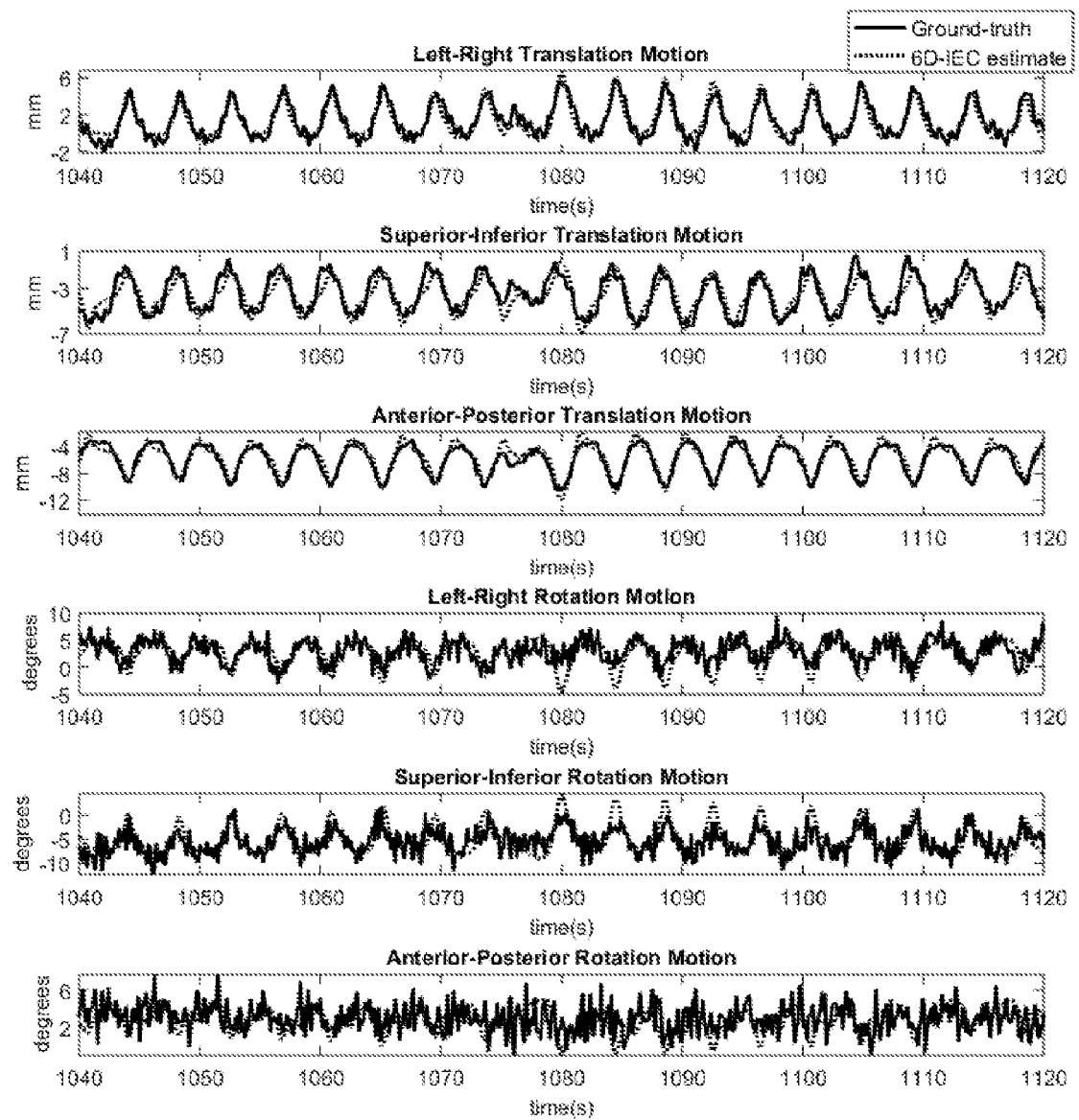
FIGS. 4A and 4B illustrates plots of two examples where 6D-IEC algorithm was successful in estimating 6DoF tumour motion during tracking with one projection every 10 seconds after an initial learning arc of 60 seconds.
Figure 4B:
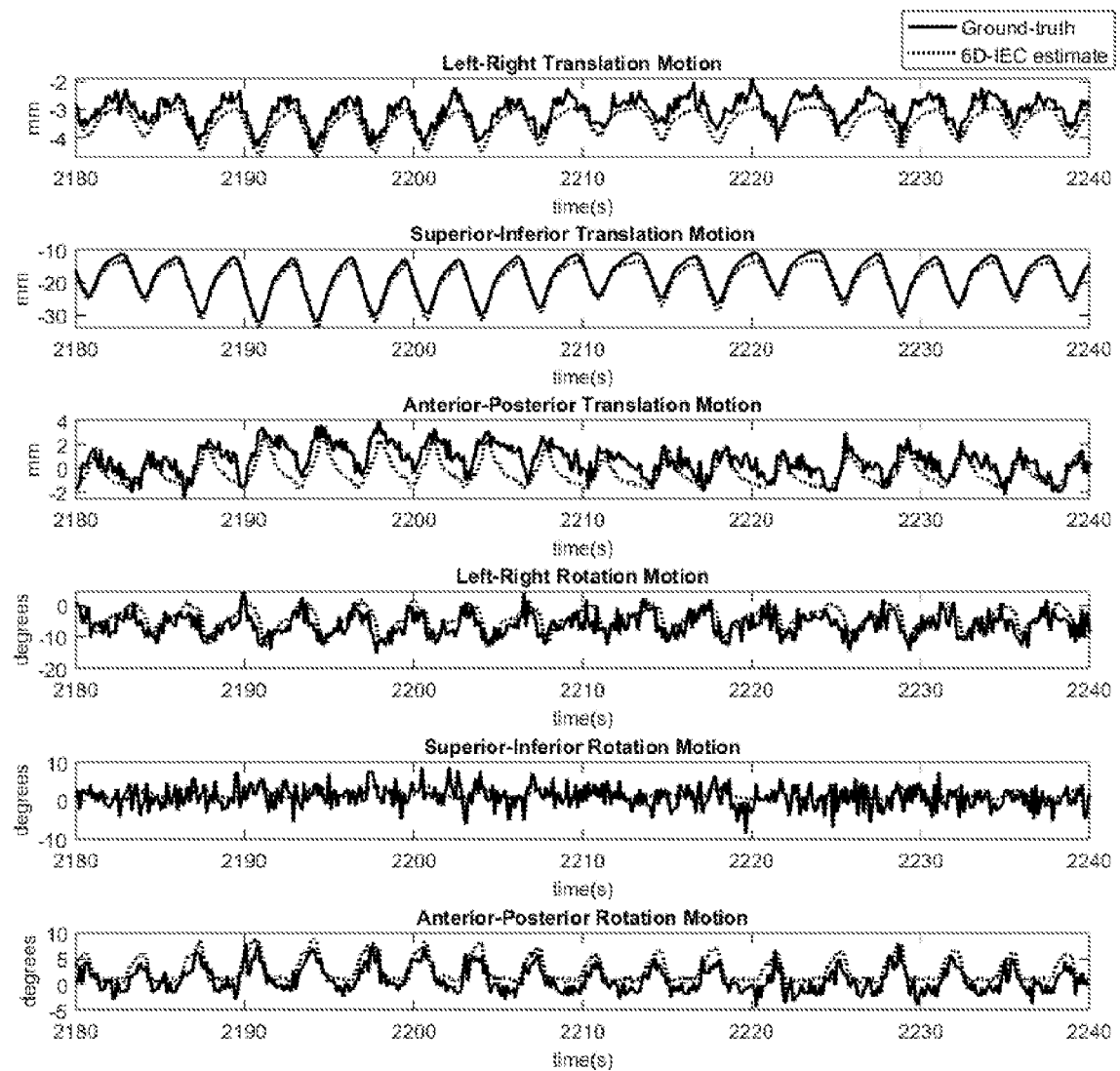

FIGS. 4A and 4B shows two cases in which 6D-IEC was successful in estimating the 6DoF motions. Two examples where the 6D-IEC algorithm was successful in estimating 6DoF tumour motion with one projection every 30 s during a slow gantry rotation VMAT treatment (1.6°/s) after an initial learning arc of 60 s. FIG. 4A shows (Patient 5, fraction 4): an example where 6D-IEC was successful in estimating tumour motion with large rotations (15° peak-to-peak in rSI), and with large translational AP (10 mm) and LR (5 mm) motion compared to SI motion. The errors in this case were: LR: 0.2±0.9 mm, SI: −0.1±0.9 mm, AP: 0.2±0.9 mm, rLR: −0.3±1.9°, rSI: 0.3±2.3° and rAP: −0.3±1.4°. FIG. 4B shows (Patient 6, fraction 1): an example where 6D-IEC was successful in estimating tumour internal 6DoF motion for the fraction with the largest intrafraction motion (20 mm in SI) in this dataset. The errors in this case were: LR: 0.3±0.3 mm, SI: −0.7±0.9 mm, AP: −0.5±1.0 mm, rLR: 2.3±2.5°, rSI: 0.48±2.04° and rAP: 1.38±1.37°.

Figure 5A:
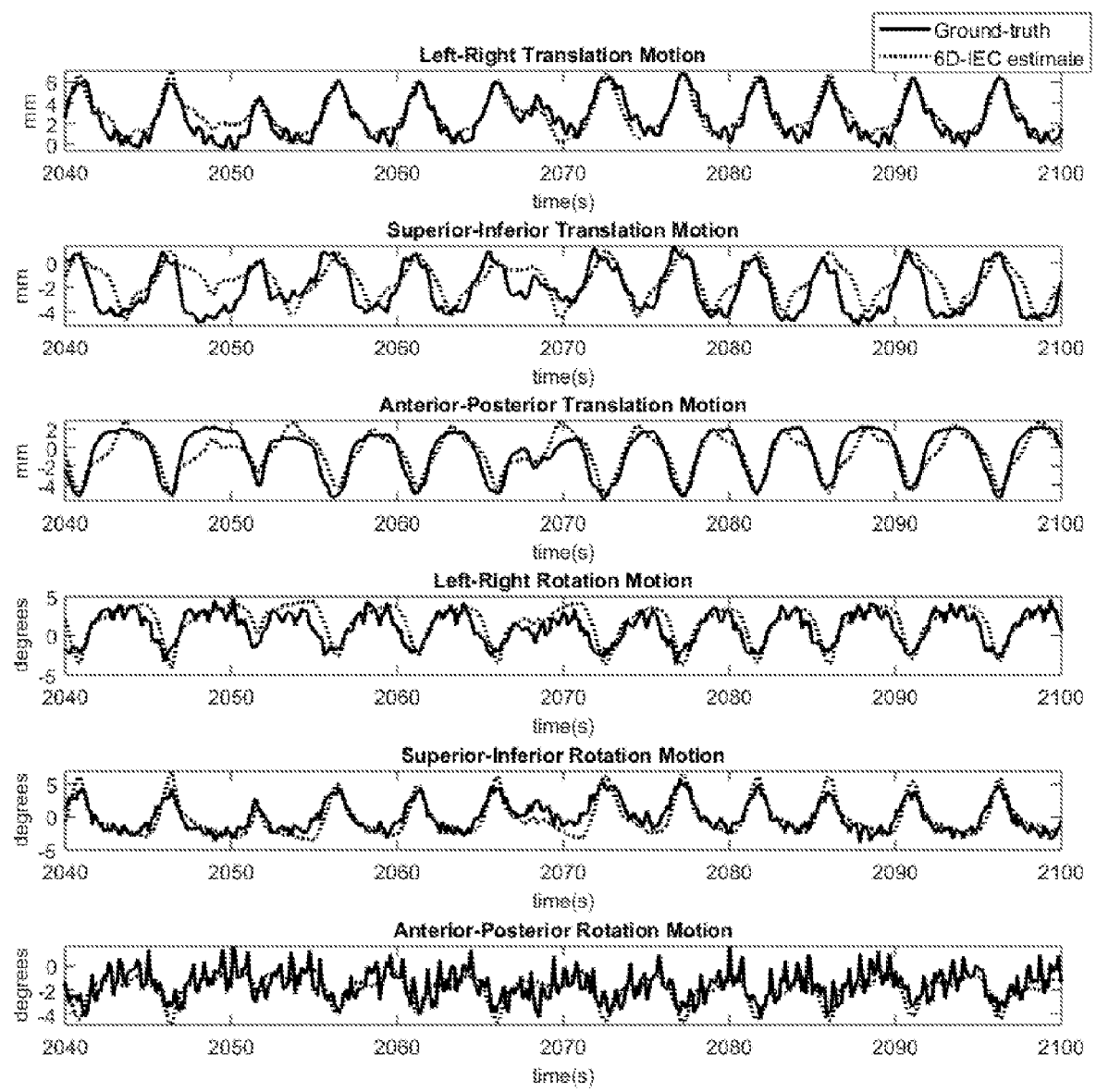
FIGS. 5A and 5B shows two further examples for the 6D-IEC algorithm in the tested dataset. Motion tracking are shown with one projection every 30 s during a slow gantry rotation VMAT treatment (1.6° s$^{-1}$) after an initial learning arc of 60 s.
Figure 5B:
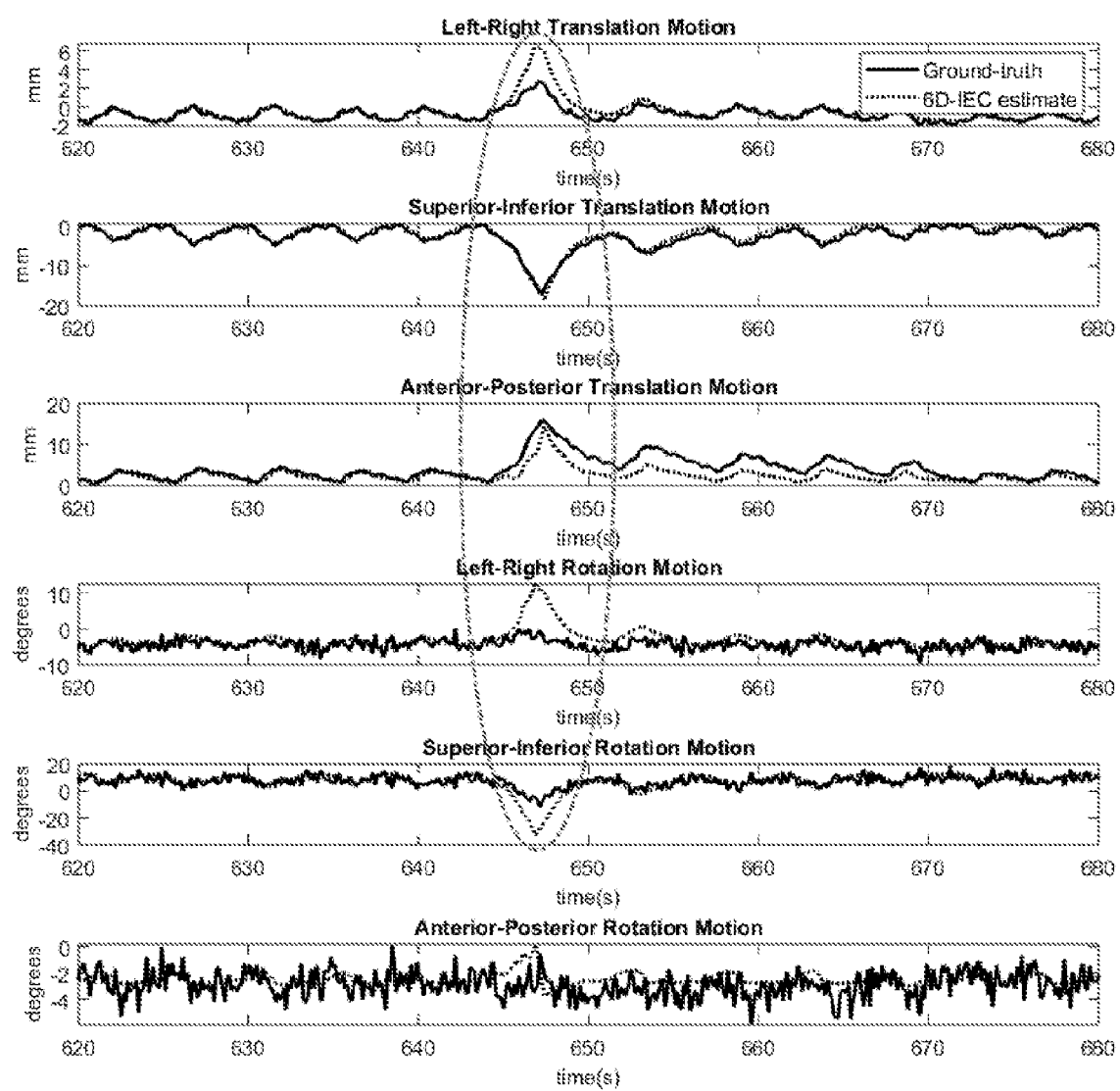

FIGS. 5A and 5B shows two further examples for the 6D-IEC algorithm in the tested dataset. Motion tracking are shown with one projection every 30 s during a slow gantry rotation VMAT treatment (1.6°/s) after an initial learning arc of 60 s. FIG. 5A shows an example (Patient 5, fraction 2) where 6D-IEC was successful in estimating translations but over-estimated rotational motion; the errors were: LR: 0.1±1.0 mm, SI: 0.4±1.3 mm, AP: 0.2±1.2 mm, rLR: 0.6±1.6°, rSI: −0.3±1.6° and rAP: −0.1±0.8°. In FIG. 5B an example (Patient 4, fraction 0) where 6D-IEC struggled due to the sudden change in correlation, leading to over-estimation of rotation during a cough (circled) followed by under-estimation of translation in the AP direction after the cough. In this case, the errors were LR: 0.0±0.3 mm, SI: −0.1±0.5 mm, AP: −1.0±1.0 mm, rLR: 0.6±1.4° rSI: 0.6±2.7°, and rAP: 0.4±0.7°.

Table 1 reports the mean and standard deviation of the difference between 6D-IEC motion estimations and the ground truth. For the gantry speed of 6°/s, across all the tested imaging update intervals, the difference in the translational motion estimation are both accurate (mean) and precise (standard deviation) to within 1 mm of Calypso while the difference in the rotation motion estimation are accurate (mean) to within 1° and precise to within 2° across all the imaging update intervals.

For the gantry speed of 1.6°/s, the largest translational errors are in the AP direction in which the standard deviation increases to 1.13 mm for the imaging update interval of 30 s while the standard deviation of the other two translation motion are all under 1 mm for all the imaging update interval. The standard deviation of AP translational errors are under 1 mm for imaging update of 1 s or lower. For the rotational estimations, the standard deviation of errors for the rotation around the SI axis (rSI) are largest at 2:31° for the imaging update of 30 s and is only under 2° for the imaging update interval of 100 ms. In all 6DoFs, the mean of estimation errors are less than 0.2 mm for translational motion and less than 0.3° for rotational motions.

The factors that could affect the accuracy and precision of 6D-IEC using the Pearson correlation test, were evaluated. The following evaluations were performed and are illustrated in FIGS. 6 to 10 including:

Range of motion in each tested patient tumour trajectory: the standard deviation of error in each degree of freedom were evaluated against the standard deviation of motion in the corresponding degree of freedom.

Motion magnitude: the estimation error at each point was evaluated against the magnitude of motion in each degree of freedom.

Correlation between external signal and internal motion in each degree of freedom: the standard deviation of error for each trace was evaluated against the correlation between each degree of freedom internal motion and the external bellows signal.

Deformation: we computed the correlation between the estimation error at each time point and the magnitude of deformation, calculated as the difference between the area of the 3D triangle formed by the 3 beacons at the same time point and at time 0 (referenced positions).

State augmentation parameter λ: we evaluated the relationship between estimation errors for each tested motion trace and the state augmentation parameter λ found for each motion trace using the aforementioned iterative method.

These tests were applied to the best and worst results of the tested clinical scenarios.

FIGS. 6-10 show the relationships between 6D-IEC errors and the different tested factors that may affect the performance of 6D-IEC in estimating 6DoF motion as scatter plots. Fitted lines are added to the scatter plot of the variable pairs with strong correlations ($\rho > 0.5$ or $\rho < -0.5$). As seen in

TABLE 1

Mean and standard deviation of error of 6D-IEC in estimating 6DoF internal tumour motion from external signal with intermittent imaging during treatment compared to the ground-truth of the signal provided from Calypso electromagnetic system.

| Clinical Scenario | Imaging Interval | LR(mm) | SI(mm) | AP(mm) | rLR(°) | rSI(°) | rAP(°) |
| --- | --- | --- | --- | --- | --- | --- | --- |
| IMRT | 0.1 s | 0.07 ± 0.58 | −0.02 ± 0.63 | 0.02 ± 0.75 | 0.12 ± 1.24 | −0.26 ± 1.75 | 0.07 ± 0.91 |
|  | 1 s | 0.09 ± 0.60 | −0.03 ± 0.70 | 0.05 ± 0.83 | 0.12 ± 1.29 | −0.27 ± 1.85 | 0.07 ± 0.92 |
|  | 3 s | 0.09 ± 0.61 | −0.04 ± 0.72 | 0.05 ± 0.87 | 0.13 ± 1.31 | −0.27 ± 1.86 | 0.08 ± 0.02 |
|  | 10 s | 0.09 ± 0.61 | −0.04 ± 0.73 | 0.05 ± 0.88 | 0.12 ± 1.31 | −0.27 ± 1.85 | 0.08 ± 0.92 |
|  | 30 s | 0.09 ± 0.61 | −0.04 ± 0.73 | 0.05 ± 0.89 | 0.12 ± 1.31 | −0.27 ± 1.87 | 0.08 ± 0.92 |
| VMAT 1.6°/s | 0.1 s | 0.04 ± 0.56 | −0.01 ± 0.63 | 0.03 ± 0.77 | 0.16 ± 1.29 | −0.26 ± 1.76 | 0.09 ± 0.88 |
|  | 1 s | 0.08 ± 0.59 | −0.03 ± 0.70 | 0.06 ± 0.84 | 0.20 ± 1.32 | −0.28 ± 1.95 | 0.11 ± 0.93 |
|  | 3 s | 0.08 ± 0.60 | −0.04 ± 0.72 | 0.06 ± 0.86 | 0.21 ± 1.33 | −0.29 ± 1.95 | 0.10 ± 0.94 |
|  | 10 s | 0.09 ± 0.60 | −0.04 ± 0.73 | 0.06 ± 0.88 | 0.21 ± 1.34 | −0.28 ± 1.98 | 0.11 ± 0.94 |
|  | 30 s | 0.09 ± 0.60 | −0.04 ± 0.73 | 0.06 ± 0.88 | 0.21 ± 1.34 | −0.28 ± 1.99 | 0.11 ± 0.95 |
| VMAT 6°/s | 0.1 s | 0.06 ± 0.56 | −0.02 ± 0.63 | 0.01 ± 0.76 | 0.14 ± 1.28 | −0.24 ± 1.84 | 0.08 ± 0.88 |
|  | 1 s | 0.08 ± 0.60 | −0.03 ± 0.69 | 0.05 ± 0.84 | 0.15 ± 1.31 | −0.27 ± 1.95 | 0.09 ± 0.92 |
|  | 3 s | 0.08 ± 0.60 | −0.04 ± 0.72 | 0.06 ± 0.86 | 0.15 ± 1.32 | −0.29 ± 1.95 | 0.09 ± 0.92 |
|  | 10 s | 0.09 ± 0.61 | −0.04 ± 0.73 | 0.06 ± 0.88 | 0.15 ± 1.32 | −0.27 ± 1.06 | 0.09 ± 0.93 |
|  | 30 s | 0.09 ± 0.61 | −0.04 ± 0.73 | 0.06 ± 0.89 | 0.15 ± 1.32 | −0.28 ± 1.95 | 0.05 ± 0.93 |

FIGS. 6 to 10, the extent to which each of the tested factors correlated with the estimating error by 6D-IEC were similar for both the best tested clinical scenario (VMAT 6°/s with 100 ms imaging update interval) and the worst tested clinical scenario (VMAT 1.6°/s with 30 s imaging update interval). Wherever there was a strong relationship, the correlation value increased slightly in the worst case.

Figure 6:
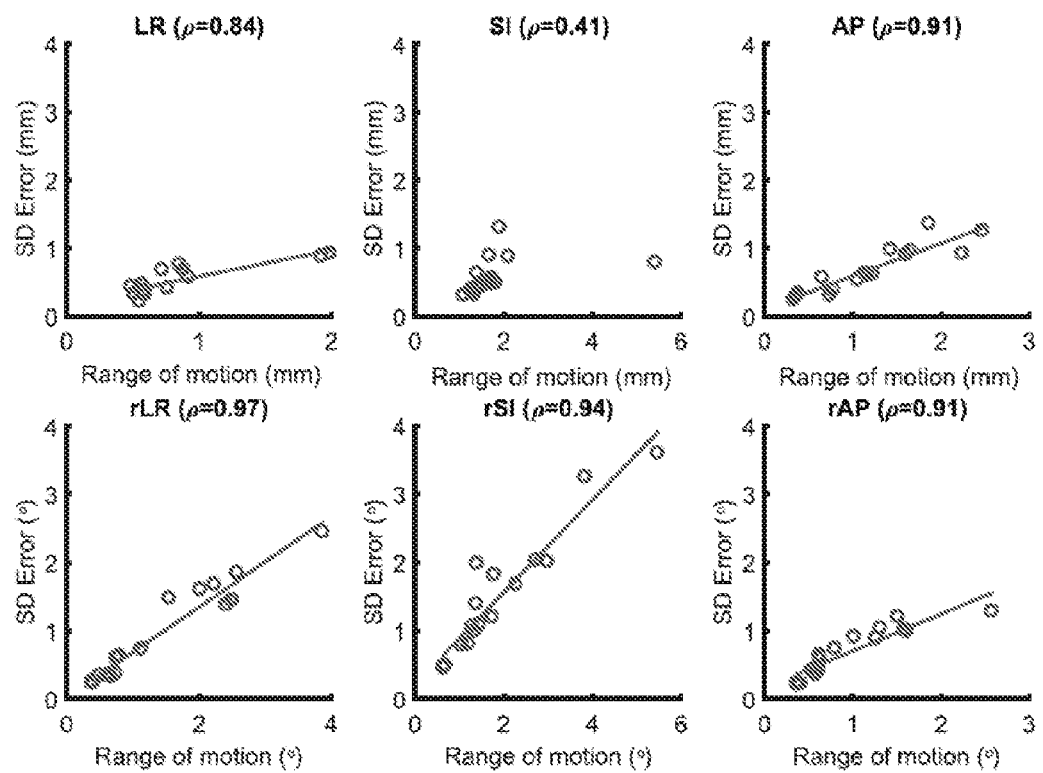
FIG. 6 shows scatter plots of the effect of the range of motion on 6D-IEC precision, measured as the standard deviation of the difference between 6D-IEC estimates and the ground-truth motion.
Figure 6:
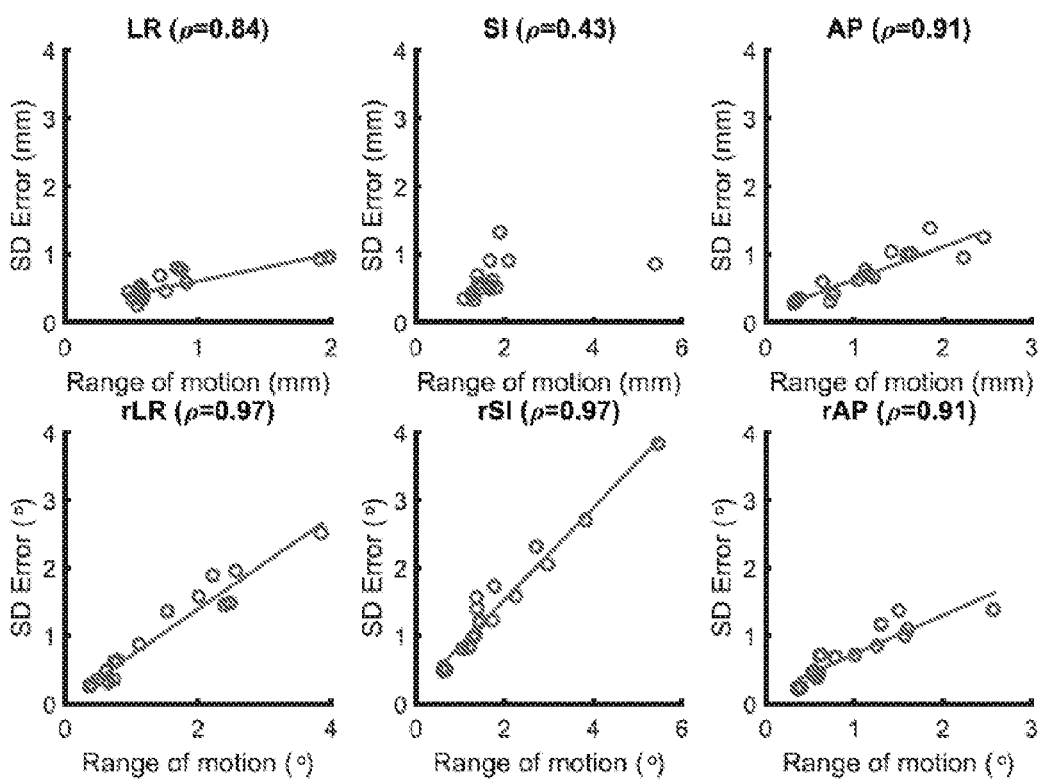

As shown in FIG. 6, there was a strong correlation between the standard deviation of error and the range of motion in each degree of freedom in the tested dataset. All of the value pairs had a Pearson correlation coefficient above 0.8, except for the SI translational motion ($\rho<0.5$). In terms of the range of motion in the tested dataset, the motion in the SI direction had the largest range for translational motion while the rotation around the SI axis had the largest motion range for rotational motion.

Figure 7:
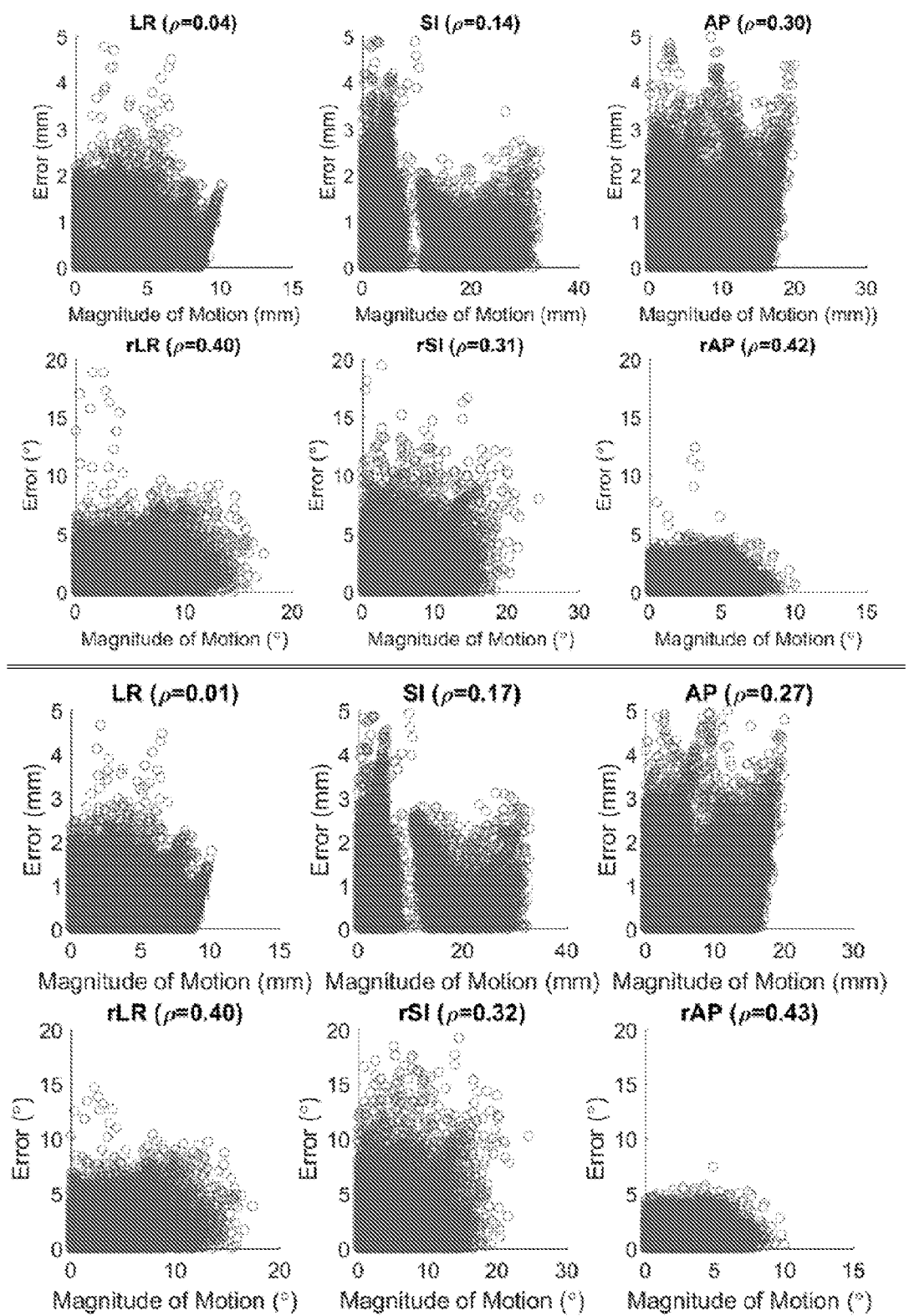
FIG. 7 shows scatter plots of the effect of the magnitude of motion on 6D-IEC performance, measured as the difference between 6D-IEC estimates and the ground-truth motion.
Figure 8:
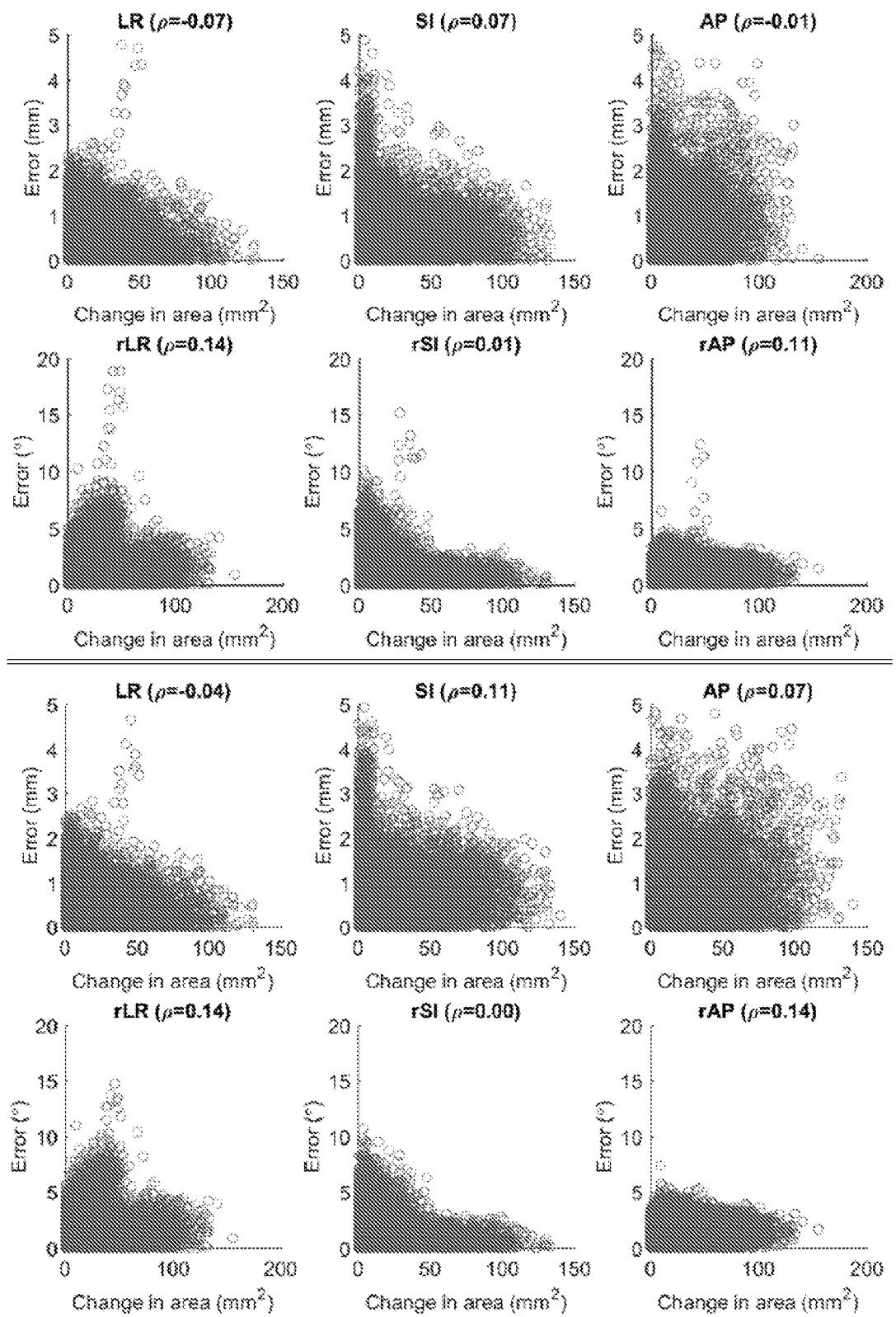
FIG. 8 shows scatter plots of the effect of deformation on 6D-IEC performance, measured as the difference between 6D-IEC estimates and the ground-truth motion. Deformation was measured as the change in the area of the 3D triangle formed by the three Calypso beacons during the tracking phase compared to their initial positions.

Although, although the estimating error of 6D-IEC increased with the motion range of each trace as evident by the high positive Pearson correlation coefficient (FIG. 6), there was no strong correlation between the estimating error magnitude and the magnitude of the motion at each time point, as shown in FIG. 7. Additionally no strong correlation was shown between the magnitude of deformation and the magnitude of error. All the Pearson correlation coefficients for this test were below 0.2 (FIG. 8).

Figure 9:
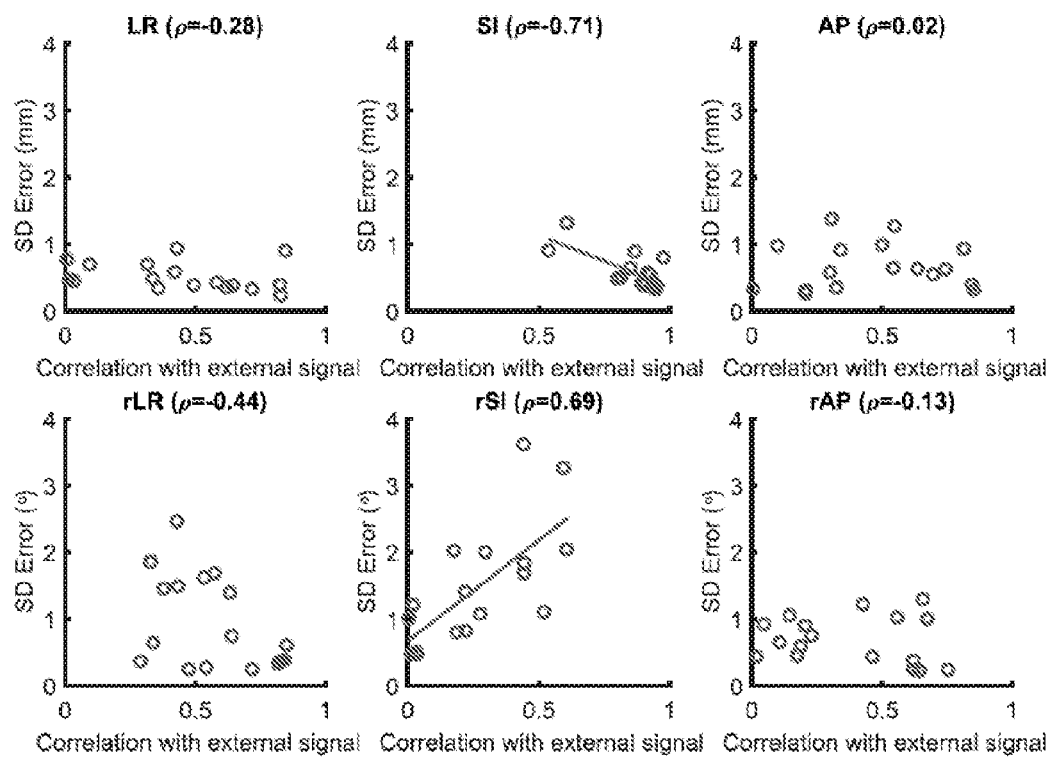
FIG. 9 shows scatter plots of the effect of the external-internal correlation on 6D-IEC precision, measured as the standard deviation of the difference between 6D-IEC estimates and the ground-truth motion.
Figure 9:
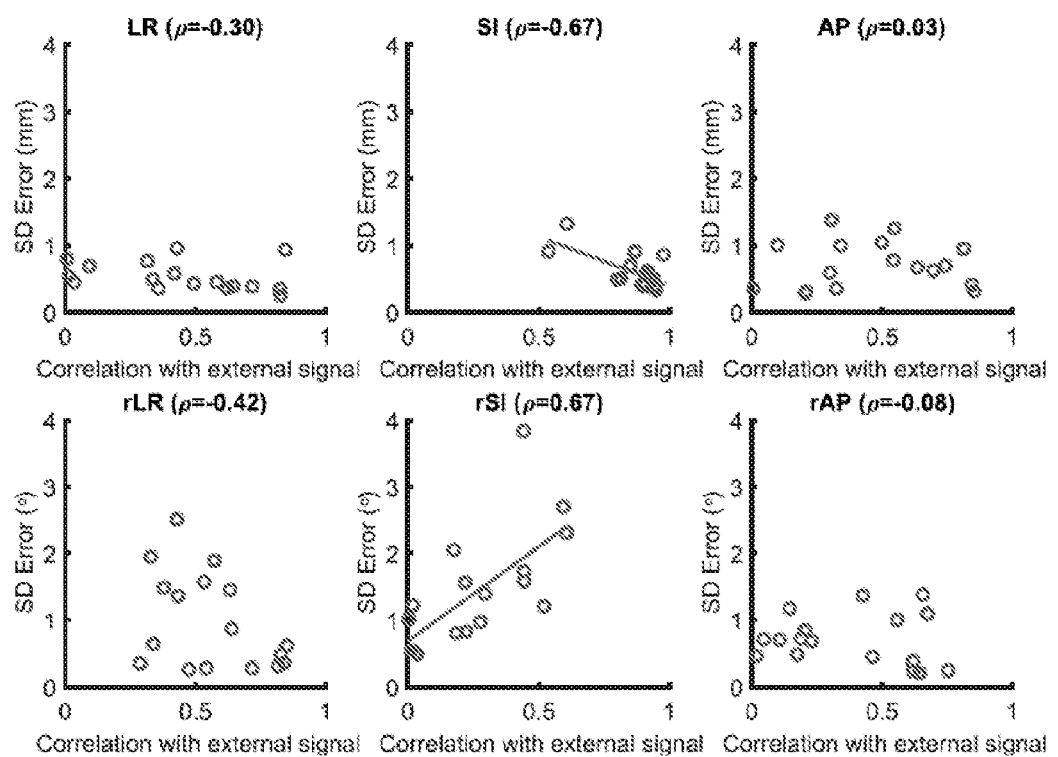
Figure 10:
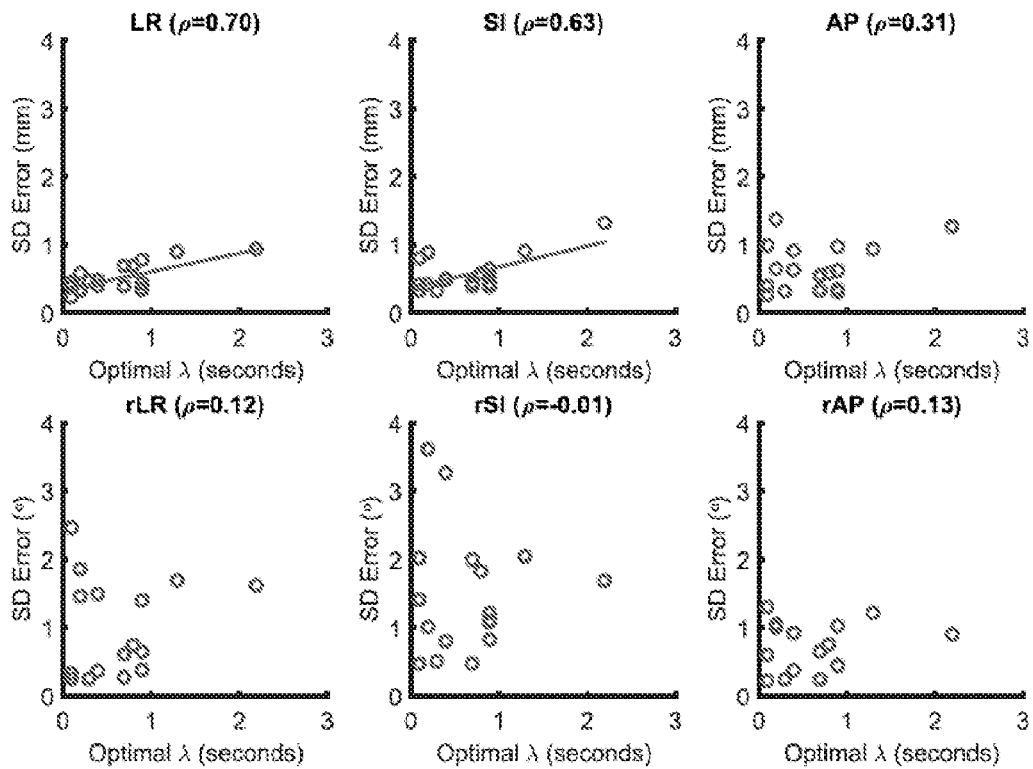
FIG. 10 shows scatter plots of the relationship between the phase augmentation parameter $\lambda$ and 6D-IEC precision, measured as the standard deviation of the difference between 6D-IEC estimates and the ground-truth motion.
Figure 10:
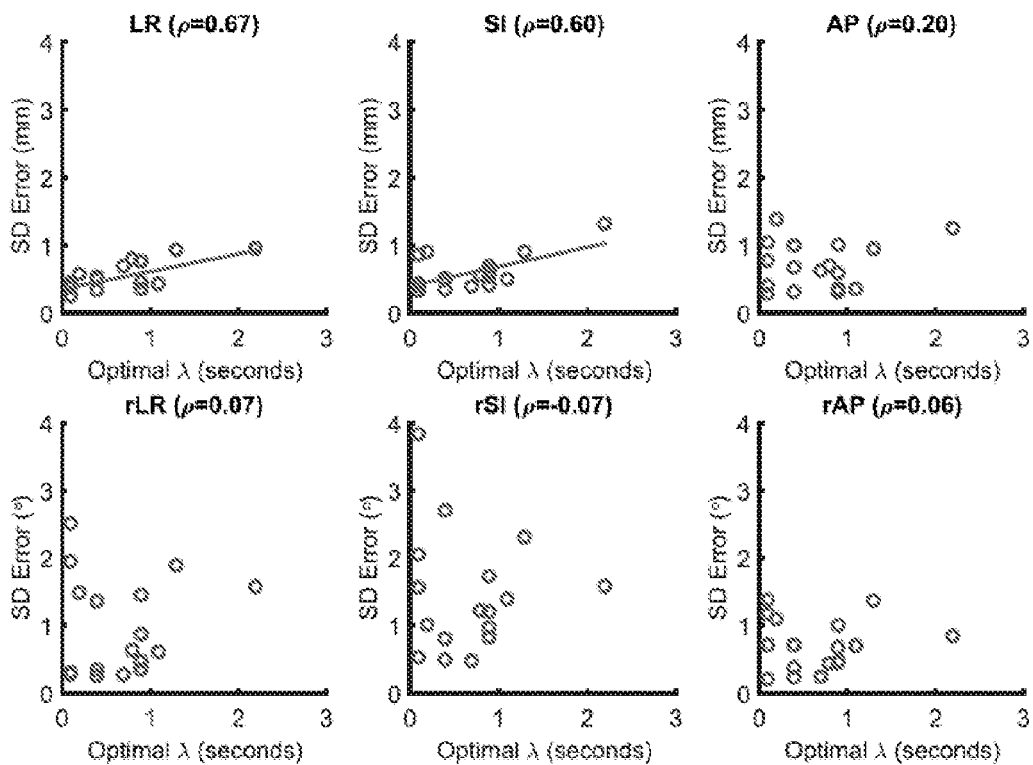

FIG. 9 shows the relationship between the standard deviation of error and the correlation between the external bellows signal and the ground-truth internal 6DoF motion. In the tested dataset, there was a strong correlation between the external signal and the internal motion in the SI direction, as evident by the clustered values of the correlation values closer to 1, than the motion in any other degree of freedom. Furthermore, there was a strong negative correlation between the standard deviation of error and the internal-external correlation value for the motion in the SI direction ($\rho=-0.7$). This strong negative correlation was not found for the motion in any other degrees of freedom for the motion. A strong positive correlation is shown between the standard deviation or error and the internal-external correlation for rotational motion around the SI axis (rSI). Notably, rotational motion round the SI axis had the lowest internal-external correlation among all the six degrees of freedom, with most of the values less than 0.5. In FIG. 10, the relationship between the optimal phase augmentation parameter ($\lambda$) and the standard deviation of 6D-IEC error in estimating the motion in each degree of freedom is depicted. As shown in FIG. 10, an increase in the ($\lambda$) value correlated with an increase in standard deviation of errors in the translational LR motion ($\rho=0.7$) and SI motion ($\rho=0.6$)) while having no discernible effect on motion in any other degrees of freedom.

The preferred embodiment of the position estimation method according to the present invention employs an external signal to estimate tumour position in 6DoF and updates the model with occasional 2D-projections of the target. Embodiments of the present invention may have the advantageous property that good positional estimation (in 6Dof) can be achieved while reducing the radiation dose to the patient compared to techniques that use continuous or rapid imaging.

It should be noted that the illustrative embodiments of the present invention describe a co-planar system geometry, in which the treatment beam and imaging beam lie in the same plane and rotate together about the target. However, as embodiments of the invention chiefly perform estimation based on the external signal (e.g. breathing signal), a non-coplanar treatment geometry, where the gantry does not rotate in an axis orthogonal to the patient's orientation, can also be used to capture the projection of the target to update the estimation algorithm.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for estimating the positon of a target in a body of a subject, comprising:
   receiving an external signal that is related to motion of the target;
   using a model of a correlation between the external signal and the motion of the target to estimate the position of the target, wherein said position estimation includes both an estimate of three dimensional location of the target and orientation of the target at the three dimensional location, whereby position is estimated for six degrees of freedom of movement of the target including both translational movement and rotational movement;
   periodically receiving a 2-dimensional projection of the target;
   updating the model of correlation between the external signal and the motion of the target based on a comparison of the estimated position of the target and the 2-dimensional projection of the target.

2. The method of claim 1 wherein periodically receiving a 2-dimensional projection of the target, includes receiving a 2-dimensional projection of the target at any one of the following intervals:
   0.1 s, 1 s, 3 s, 10 s, 30 s, an interval greater than 0.1 s, an interval greater than 1 s, an interval greater than 3 s, an interval greater than 10 s, an interval greater than 30 s.

3. The method of claim 1 further comprising:
   determining the correlation between the external signal and the motion of the target to enable estimation of the position of the target by:
      receiving a series of 2-dimensional projections captured at a rate equal to or higher than the periodically received 2-dimensional projection of the target;
      receiving an external signal that overlaps in time with at least part of the received series of 2-dimensional projections;
      determining a correlation between the external signal at a time (t) and a three dimensional location and orientation of the target from a plurality of said 2-dimensional projections.

4. The method of claim 3 wherein the successive projections in the series of 2-dimensional projections are captured at an interval being any one of the following:
   an interval less than 0.1 s, 0.1 s, an interval less than 1 s.

5. The method of claim 1 wherein the external signal represents respiration of the subject.

6. The method of claim 5, wherein the external signal is derived from any one or more of the following:
   respiratory monitor outputting a signal from an external surface or volumetric signal;
   optical surface monitoring device;
   a bellows belt.

7. The method of claim 1 wherein the 2-dimensional projection is an x-ray image of at least part of a subject and includes the target.

8. The method of claim 1 wherein a three dimensional location and orientation of the target from a plurality of said 2-dimensional projection is determined by:

identifying one or more markers positioned with respect to the target to facilitate identification of the target in a 2-dimensional projection.

9. The method of claim 1 wherein a three dimensional location and orientation of the target from a plurality of said 2-dimensional projections is determined by identifying one or more landmarks to facilitate identification of the target in a 2-dimensional projection.

10. The method of claim 9 wherein the at least three markers are identified.

11. A method of guided radiation therapy in which at least one beam of radiation is directed at a target, comprising:
  estimating the positon of the target using a method as claimed in claim 1, and
  directing the beam based on the estimated position.

12. The method of claim 11 further comprising tracking the target by successively performing a method of estimating the position of the target, and directing the beam at the target based on said tracking.

13. The method of claim 11 wherein directing the beam based on the estimated portion includes adjusting or setting one or more of the following system parameters:
  at least one geometrical property of said at least one emitted beam;
  a position of the target relative to the beam;
  a time of emission of the beam; and
  an angle of emission of the beam relative to the target about the system rotational angle.

14. A system for guided radiation therapy, comprising:
  a radiation source for emitting at least one treatment beam of radiation;
  an imaging system arranged to generate a succession of images comprising a two dimensional projection of a field of view and in which the location of the target may be identified;
  a monitoring system arranged to sense from the subject a parameter that is related with motion of the target, and output an external signal that is related with motion of the target; and
  a control system to direct the at least one treatment beam at the target, wherein said beam control system is configured to:
    receive images from the imaging system and the external signal; and estimate the position of the target using a method as claimed in claim 1; and
    adjust the system to direct the at least one beam at the target.

15. The system as claimed in claim 14 wherein the radiation source is configured to direct a treatment beam along a first beam axis, and the imaging system includes a second radiation source configured to emit at least one imaging beam along a second beam axis that is orthogonal to the first direction and a radiation detector configured to detect radiation transmitted through the target to generate a projection of said at least one imaging beam in a plane normal to the direction of emission of the at least one imaging beam.

16. The system as claimed in claim 15 configured for rotating the radiation source and imaging system about a system rotational axis that is orthogonal to the first and second direction to enable sequential treatment and imaging of the subject at different angular positions about the system rotational axis.

17. The system of claim 14 further comprising a support platform on which a subject of radiation therapy is supported during treatment, at a location such that the centroid of the target is substantially aligned with the intersection between the system rotational axis, and the first and second beam axes.

18. The system of claim 14 wherein the control system controls one or more of:
  at least one geometrical property of said at least one emitted beam;
  a position of the target relative to the beam;
  a time of emission of the beam; and
  an angle of emission of the beam relative to the target about the system rotational angle.

19. The system of claim 14 further comprising a respiration monitor to provide the external signal.

* * * * *